United States Patent [19]
Robinson et al.

[11] Patent Number: 5,489,743
[45] Date of Patent: Feb. 6, 1996

[54] TRANSGENIC ANIMAL MODELS FOR THROMBOCYTOPENIA

[75] Inventors: Murray O. Robinson, Malibu; Pamela Hunt; Robert A. Bosselman, both of Thousand Oaks, all of Calif.

[73] Assignee: Amgen Inc., Thousand Oaks, Calif.

[21] Appl. No.: 6,082

[22] Filed: Jan. 19, 1993

[51] Int. Cl.⁶ .......................... A01K 67/00; C12N 15/37; C12N 15/90
[52] U.S. Cl. ...................... 800/2; 800/DIG. 1; 435/172.1; 435/172.3; 435/320.1; 536/23.72; 536/24.1
[58] Field of Search .................. 536/23.1, 23.72, 536/24.1; 435/172.1, 172.3, 240.1, 240.2, 320.1; 800/2, DIG. 1; 535/6, 12, 22, 53, 70

[56] References Cited

U.S. PATENT DOCUMENTS

| | | | |
|---|---|---|---|
| 4,736,866 | 4/1988 | Leder | 800/2 |
| 4,870,009 | 10/1989 | Evans | 435/70 |
| 4,873,191 | 10/1989 | Wagner | 435/172.3 |
| 5,162,215 | 11/1992 | Bosselman | 435/172.3 |
| 5,175,383 | 12/1993 | Leder | 800/2 |
| 5,175,384 | 12/1993 | Krimpenfont | 800/2 |
| 5,175,385 | 12/1993 | Wagner | 800/2 |

FOREIGN PATENT DOCUMENTS

WO91/13150 9/1991 WIPO.
WO92/06190 4/1992 WIPO.

OTHER PUBLICATIONS

Al–Ubaidi et al. Proc. Nat'l Acad. Sci. USA 89: 1194–98 (1992).
Ravid et al. Mol. Cell. Biol. 11:6116–6127 (1991).
Ravid et al. Proc. Nat'l Acad. Sci. USA 88:1521–1525 (1991).
Jat et al. Proc. Nat'l Acad. Sci. USA 88:5096–5100 (1991).
Palmiter et al. Nature 316: 457–460 (1985).
Richie et al. Nature 312: 517–520 (1984).
Brinster et al. Cell 37:367–379 (1984).
Stewart et al. Cell 38: 627–637 (1984).
Gordon et al. Proc. Nat'l Acad. Sci. USA 77:7380–7384 (1980).
Marquerie et al. 7th Int'l Symposium on the Biology of Vascular Cells, p. 18 (1992).
Wendling et al. Blood 80:246a, abstract #973 (1992).
Mignotte et al. Blood 80: 245a, abstract #972 (1992).
Uzan et al. J. Biol. Chem. 266:8932–8939 (1991).
Wenger et al. Biochem. Biophys. Res. Comm. 156:389–395 (1988).
Gerwitz & Hoffman–Chapter 15 in: Hematology: Basic Principles and Practice, pp. 205–210, Churchill–Livingstone Publishers, N.Y. (1991).
Gerwitz & Poncz–Chapter 88 in: Hematology, Basic Principles and Practice, pp. 1148–1157, Churchill–Livingstone Publishers, N.Y. (1991).
George et al. in : Hematology, 4th edition, pp. 1343–1351, McGraw Hill Publishers, N.Y. (1990).
Hoffman, Blood 74: 1196–1212 (1989).
Mazur, Exp. Hematol. 15: 340–350 (1987).
Hunt et al. Blood 80: 904–911 (1992).
Williams Exp. Hematol. 19: 714–718 (1991).
Peters et al. Blood 76: 745–754 (1990).
Jackson, Blood Cells 15: 237–253 (1989).
Dowton et al. Blood 65: 557–563 (1985).
Radley et al. Blood 55: 164–166 (1980).
DeCaprio et al. Cell 54: 275–283 (1988).
Burstein et al. J. Cell Physiol. 122: 159–165 (1985).
GT Diamandopoulos (1972) Science 176: 173–175.

Primary Examiner—Jacqueline M. Stone
Assistant Examiner—Bruce R. Campbell
Attorney, Agent, or Firm—Nancy Oleski

[57] ABSTRACT

Transgenic mice and methods of preparing such mice are disclosed. The mice exhibit decreased platelet counts and/or megakaryocyte leukemia.

5 Claims, 7 Drawing Sheets

FIG. 2

```
5'  TTGGAGCTCC ACCGCGGTGG CGGCCGCTCT AGAACTAGTG GATCCCCCGG
    GCTGCAGGAA TTCGATAATT CCTTTACTCT GCGAATGCTG AAATCTTTGG
    TGAAGGTGGC ACAGAAGAGT TTTCTTGCTG TCCAGATTAA AATCCTCTTA
    TCATATATAT ATATATATAT ATATATATAT GTATATATAT ATATTTATTT
    TTTTATTTTT ATTTTTTTTT TTTTTTGCTG ACCCAGCCGA GGCCTTGAGT
    TTCAGTTCCC TAAAGGCATA GGGATTCTGA CATGTTTTGC AGTAGCCGTT
    GTTGTCCATG CTGAGTGTCC ATAAATGTAT GCCCCGGGGA GTTATGCTTG
    ACTATATCAC TATGCATGGG GGGCAGATAA AGGGCACAT AATTATAACC
    ATATATGGCA TGAATTAATA TAGAGATCTC CAACTGTCCC AGAAAGCTTT
    CTTCTCTACT CTTCTCCAGG GTAGAGCTGA GCAGACTAAA AGATTTTTAT
    CAAAGAAAAG CCTTCAAATA CTACCTCAGG GATGTTTCTA AAGAGTCCTG
    AGAAGAGCAG ACCCTGCCGC CTCCAGTAGA TTGGACAGCC GTAGCTCAGA
    AGAGCCTCCA GAATTTCCTG CAGGAGGCTT CGGAAGGTTT CCATCGTGAG
    GATGAAAGTC AGAAGCCATT GCCTAGCCAT TCACTTCAAT GTTTTAATGG
    CAGAAAATAA ATTTCCAGTC TCGCATCTCT AACCACATGG CAGTCAAACT
    CACAGCAAAT CAACAGGAAG CACGGCAGGG TGTTTGGGGT AGGGCAACCG
    GAAGTCGGGA AGGCAACAAA TTGGTACTGA AGGTGCATGT TCTGTAAACC
    GCATGGGGAT AGCAGAAAAT TCTCTGCCAC ATACAGCATA CCTTCTGCGA
    AAATTCCAAC TGTTTCTACC TCTGTAGACT GTTCACATAA ATTCACATTG
    GGGACGTGGA TCCTGCTGAC AGCTGCTGAC AGCTGGCCTC AGCTGCTGCT
    TCTTCTTCTT CTTCTTTTTT TTTTTTTTTT TTTCCTGTTC TATGTTGCTT
    TAATCTTGGC TGGCCAGATC TCAAGTACTG TTCCACAAGT GTCATTGCTT
    CTGTGGATCA CTTCCTCATC CCCTATCCCG GGTTTCCGGA CTGGGCTGGC
    AGTGAAGATA AAACGTGTCT AGAAAGTCAC AGGAGCCACT GTCTGGCACT
    TAGAGCCCCA GACCCCAGTT TCCCCGAGGT AGCCCTTGGA TATCAAGCTT
    GAATTATCAA GCTT     3'
```

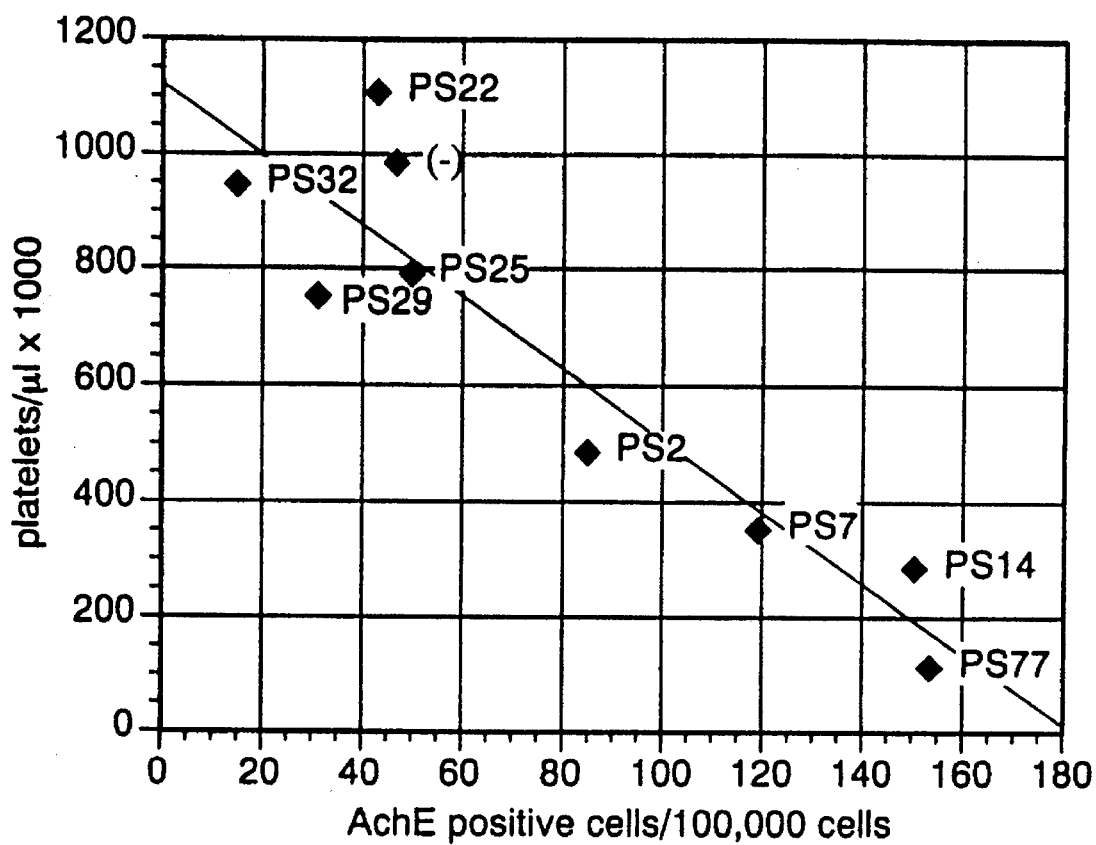

FIG. 4A

5'  AATTCCTTTACTCTGCGAATGCTGAAATCTTTGGTGAAGGTGGCACAGAA
    ||||||||||||||||||||||||||||||||||||||||||||||||||
    AATTCCTTTACTCTGCGAATGCTGAAATCTTTGGTGAAGGTGGCACAGAA

GAGTTTTCTTGCTGTCCAGATTAAAATCCTCTTATCATATATATATATAT
    ||||||||||||||||||||||||||||||||||||||||||||||| |||
    GAGTTTTCTTGCTGTCCAGATTAAAATCCTCTTATCATATATATATGTAT

ATATATATATATATGTATATATATATATTTATTTTTTATTTTTATTTTT
    |||||||||||||| ||||||||||          |||| ||||| |||||
    ATATATATATATATATATATATA.........TTTTTTTTTTTTTTT

TTTTTTTTTGCTGACCCAGCCGAGGCCTTGAGTTTCAGTTCCCTAAAGG
    |||||||||||||||||||||||||||||||||||||||||||||||||
    TTTTTTTTTGCTGACCCAGCCGAGGCCTTGAGTTTCAGTTCCCTAAAGG

CATAGGGATTCTGACATGTTTTGCAGTAGCCGTTGTTGTCCATGCTGAGT
    ||||||||||||||||||||||||||||||||||||||||||||||||||
    CATAGGGATTCTGACATGTTTTGCAGTAGCCGTTGTTGTCCATGCTGAGT

GTCCATAAATGTATGCCCCGGGGAGTTATGCTTGACTATATCACTATGCA
    ||||||||||||||||||||||||||||||||||||||||||||||||||
    GTCCATAAATGTATGCCCCGGGGAGTTATGCTTGACTATATCACTATGCA

TGGGGGGCAGATAAAGGGGCACATAATTATAACCATATATGGCATGAATT
    ||||||||||||||||||||||||||||||||||||||||||||||||||
    TGGGGGGCAGATAAAGGGGCACATAATTATAACCATATATGGCATGAATT

AATATAGAGATCTCCAACTGTCCCAGAAAGCTTTCTTCTCTACTCTTCTC
    ||||||||||||||||||||||||||||||||||||||||||||||||||
    AATATAGAGATCTCCAACTGTCCCAGAAAGCTTTCTTCTCTACTCTTCTC

CAGGGTAGAGCTGAGCAGACTAAAAGATTTTTATCAAAGAAAAGCCTTCA
    ||||||||||||||||||||||||||||| ||||||||||||||||||||
    CAGGGTAGAGCTGAGCAGACTAAAAGA.TTTTATCAAAGAAAAGCCTTCA

AATACTACCTCAGGGATGTTTCTAAAGAGTCCTGAGAAGAGCAGACCCTG
    ||||||||||||||||||||||||||||||||||||||||||||||||||
    AATACTACCTCAGGGATGTTTCTAAAGAGTCCTGAGAAGAGCAGACCCTG

CCGCCTCCAGTAGATTGGACAGCCGTAGCTCAGAAGAGCCTCCAGAATTT
    ||||||||||||||||||||||||||||||||||||||||||||||||||
    CCGCCTCCAGTAGATTGGACAGCCGTAGCTCAGAAGAGCCTCCAGAATTT

CCTGCAGGAGGCTTCGGAAGGTTTCCATCGTGAGGATGAAAGTCAGAAGC
    ||||||||||||||| ||||||||||||||||||||||||||||||||||
    CCTGCAGGAGGCTTCAGAAGGTTTCCATCGTGAGGATGAAAGTCAGAAGC

CATTGCCTAGCCATTCACTTCAATGTTTTAATGGCAGAAAATAAATTTCC
    ||||||||||||||||||||||||||||||||||||||||||||||||||    3'
    CATTGCCTAGCCATTCACTTCAATGTTTTAATGGCAGAAAATAAATTTCC

FIG. 4B

```
5'  AGTCTCGCATCTCTAACCACATGGCAGTCAAACTCACAGCAAATCAACAG
    ||||  |||||||||||||||||||||||||||||||||||||||||||||
    AGTCACGCATCTCTAACCACATGGCAGTCAAACTCACAGCAAATCAACAG

G.AAGCACGGCAGGGTGTTTGGGGTAGGGCAACCGGAAGTCGGGAAGGCA
    |  |||||||||||||||||||||||| ||||||||||||||||||||||
    GAAAGCACGGCAGGGTGTTTGGGGTCGGGCAACCGGAAGTCGGGAAGGCA

ACAAATTGGTACTGAAGGTGCATGTTCTGTAAACCGCATGGGGATAGCAG
    ||||||||||||||||||||||||||||||||||||||||||||||||||
    ACAAATTGGTACTGAAGGTGCATGTTCTGTAAACCGCATGGGGATAGCAG

AAAATTCTCTGCCACATACAGCATACCTTCTGCGAAAATTCCAACTGTTT
    ||||||||||||||||||||||||||||||||||||||||||||||||||
    AAAATTCTCTGCCACATACAGCATACCTTCTGCGAAAATTCCAACTGTTT

CTACCTCTGTAGACTGTTCACATAAATTCACATTGGGGACGTGGATCCTG
    ||||||||||||||||||||||||||||||||||||||||||||||||||
    CTACCTCTGTAGACTGTTCACATAAATTCACATTGGGGACGTGGATCCTG

CTGACAGCTGCTGACAGCTGGCCTCAGCTGCTGCTTCTTCTTCTTCTTCT
    |||||||||||||||||||||||||||||||| ||         || || |
    CTGACAGCTGCTGACAGCTGGCCTCAGCTGCTTCT........TTTTTT

TTTTTTTTTTTTTTTTCCTGTTCTATGTTGCTTTAATCTTGGCTGGCC
    ||||||||||||||||||||||||||||||||||||||||||||||||
    TTTTTTTTTTTTTTTTCCTGTTCTATGTTGCTTTAATCTTGGCTGGCC

AGATCTCAAGTACTGTTCCACAAGTGTCATTGCTTCTGTGGATCACTTCC
    ||||||||||||||||||||||||||||||||||||||||||||||||||
    AGATCTCAAGTACTGTTCCACAAGTGTCATTGCTTCTGTGGATCACTTCC

TCATCCCCTATCCCGGGTTTCCGGACTGGGCTGGCAGTGAAGATAAAACG
    ||||||||  ||||||||||||||||||||||||||||||||||||||||
    TCATCCCC.ATCCCGGGTTTCCGGACTGGGCTGGCAGTGAAGATAAAACG

TGTCTAGAAAGTCACAGGAGCCACTGTCTGGCACTTAGAGCCCCAGACCC
    ||||||||||||||||||||||||||||||||||||||||||||||||||
    TGTCTAGAAAGTCACAGGAGCCACTGTCTGGCACTTAGAGCCCCAGACCC

CAGTTTCCCCG
    |||||||||||    3'
    CAGTTTCCCCG
```

TRANSGENIC ANIMAL MODELS FOR THROMBOCYTOPENIA

BACKGROUND OF THE INVENTION

1. Field of the Invention

This invention relates to mammals into which foreign DNA has been introduced, thereby generating transgenic mammals. More specifically, the invention concerns generation of transgenic mammals that have a decreased platelet count, megakaryocyte leukemia, or both conditions.

2. Description of Related Art

Production of transgenic mammals involves the insertion of novel nucleic acid sequences into one or more chromosomes of the mammal. The DNA is typically delivered to the pronucleus of an egg where it is incorporated into the DNA of the embryo. This embryo is then implanted into a "surrogate host" for the duration of gestation. The offspring of the surrogate host are evaluated for the presence of the novel nucleic acid sequence(s).

Expression of the novel DNA sequence(s), or transgene(s), can confer a new phenotype on the mammal. Depending upon the nucleic acid sequence(s) inserted and the level of expression in the mammal, the mammal may become more or less susceptible to a particular disease or series of diseases. Such transgenic mammals are valuable for in vivo screening and testing of compounds that may be useful in treating or preventing the disease(s), and/or for developing methods useful in diagnosing the disease.

Transgenic mammals have been described in the art. Wagner et al., U.S. Pat. No. 4,873,191 teach mammals containing exogenous DNA which has been introduced by microinjection of the DNA into a mammalian zygote.

Leder et al., U.S. Pat. No. 4,736,866, teach a transgenic mammal whose germ and somatic cells contain an activated oncogene sequence introduced into the mammal, or its ancestors, early in development (the one-cell or fertilized embryo stage). Such transformation results in the animal having a greater than normal chance of developing neoplasms.

Evans et al., U.S. Pat. No. 4,870,009, teach production of certain mammalian hormones by insertion of a DNA construct into fertilized mammalian eggs and implanting the fertilized eggs into a host mother for gestation. The DNA construct comprises a mammalian metallothionein gene promoter sequence fused to the mammalian hormone sequence of interest. The blood of the transformed mammals then is collected and the hormone of interest is isolated.

Noble et al., WO 91/13150, published Sep. 5, 1991, and Jat et al., *Proc. Nat'l. Acad. Sci. USA*, 88:5096–5100 [1991], teach production of mice with a DNA construct that contains a mutant SV40 large T antigen gene (the SV40 tsA58 mutant) linked to a major histocompatibility complex I promoter (H-2Kb). The specific promoter is used to facilitate expression of the transgene in a wide variety of tissues, and is induced by certain interferons. These mice are used as a source for generating transformed cell lines.

Leder et al., U.S. Pat. No. 5,175,383, describe a male transgenic mouse expressing the int-2 gene in urogenital tissues resulting in benign prostatic hyperplasia or hypertrophy.

Krimpenfort et al., U.S. Pat. No. 5,175,384, describe a transgenic mouse with a decreased level of mature T-cells.

Wagner et al., U.S. Pat. No. 5,175,385, describe a transgenic mouse expressing the human beta-interferon gene.

Ravid et al., *Proc. Nat'l. Acad. Sci. USA*, 85:1521–1525 [1991], discuss mice containing a transgene construct containing the platelet factor 4 promoter ("PF4") linked to the beta-galactosidase gene, and Ravid et al., *Mol. Cell Biol.*, 11:6116–6127 [1991], teach various domains of the PF4 promoter.

Palmiter et al., *Nature* 316:457–460 [1985], teach the formation of choroid plexus tumors in mice that contain the DNA sequence for the 72 base-pair repeat SV40 enhancer and large-T antigen. When the SV40 enhancer element is not included in the DNA construct, other pathologies are observed as well.

Brinster et al., *Cell* 37:367–79 [1984], teach production of mice with a construct containing the SV40 early region genes and a metallothionein fusion gene. Several of the mice developed choroid plexus tumors, and/or thymic hypertrophy.

Thrombocytopenia, a decreased level of platelets in the blood relative to normal levels for a given mammalian species, affects the blood clotting ability of afflicted individuals. One manifestation of this disorder is increased bleeding. In addition, thrombocytopenia is a common side effect in patients receiving chemotherapy. The only currently available method for treating the disorder is platelet transfusion, a difficult and inherently risky procedure.

Jackson, *Blood Cells*, 15:237–253 [1989] describes a rat strain with a reduced platelet number.

Peters et al., *Blood*, 76:745–754 [1990] describe an autosomal recessive mutation in mice that confers combined anemia and thrombocytopenia on afflicted mice.

Megakaryocyte leukemia is a condition characterized by production of cancerous cells that have phenotypic traits resembling megakaryocytes. Such leukemia is currently treated by bone marrow transplants.

In view of the devastating effects of thrombocytopenia and megakaryocyte leukemia, there is a need in the art for suitable animals that provide in vivo model systems for studying the diseases and compounds that can be used to treat and/or prevent the diseases.

Accordingly, it is an object of the invention to provide a transgenic mammal that has a genotype which confers an increased proclivity towards thrombocytopenia and/or megakaryocyte leukemia as compared to a non-transgenic mammal. Such mammals are useful in screening compounds for treating these diseases, and for other purposes.

It is a further object herein to provide methods for preparing, and to prepare transgenic mammals containing such genotypes.

Other such objects will readily be apparent to one of ordinary skill in the art.

SUMMARY OF THE INVENTION

This invention is based on the unexpected discovery that transgenic mice containing a nucleic acid construct encoding the SV40 early region tsA58 mutant regulated by the rat PF4 promoter unexpectedly develop varying levels of thrombocytopenia and/or megakaryocyte leukemia. In accordance with this invention, the mice present a novel and useful system for screening compounds useful for treating and/or preventing these diseases.

In one preferred embodiment of the invention, a mammal containing a transgene and its progeny are provided.

In another preferred embodiment, a mouse containing a transgene and its progeny are provided.

In still another preferred embodiment, there is provided a method of preparing a mammal with a decreased platelet level as compared to normal platelet counts for that species of that mammal which comprises:

(a) introducing into a fertilized embryo a vector comprising nucleic acid encoding the SV40 early region tsA58 mutant operably linked to a platelet precursor or megakaryocyte promoter; and (b) implanting the transformed embryo in a surrogate host. In an additional aspect of this embodiment of the invention, the offspring can be screened for decreased platelet counts.

In yet another preferred embodiment, there is provided a method of preparing mammals exhibiting megakaryocyte leukemia which comprises:

(a) introducing into an embryo a vector comprising a nucleic acid sequence encoding the SV40 early region tsA58 mutant operably linked to a platelet precursor or megakaryocyte promoter; and, (b) implanting the transformed embryo into a surrogate host. The offspring can be screened for megakaryoctye leukemia.

In other preferred embodiments, cell lines derived from certain tissues of the transgenic mammals such as bone marrow, lymph node and spleen are provided.

BRIEF DESCRIPTION OF THE DRAWINGS

FIG. 2 depicts the nucleic acid sequence of a Sprague-Dawley rat PF4 promoter as originally sequenced(SEQ ID NO:1).

FIG. 3C shows acetylcholinesterase activity (a marker for megakaryocytes) versus platelet count in F1 mice.

FIGS. 4A–4B depicts a comparison of the Fisher rat (bottom sequence SEQ ID NO:5) and Sprague-Dawley rat (top sequence SEQ ID NO:4) PF4 promoter sequences. The sequences have been aligned in a manner to maximize their homology. The nucleic acid sequence differences are indicated.

DETAILED DESCRIPTION OF THE INVENTION

Figure 1:
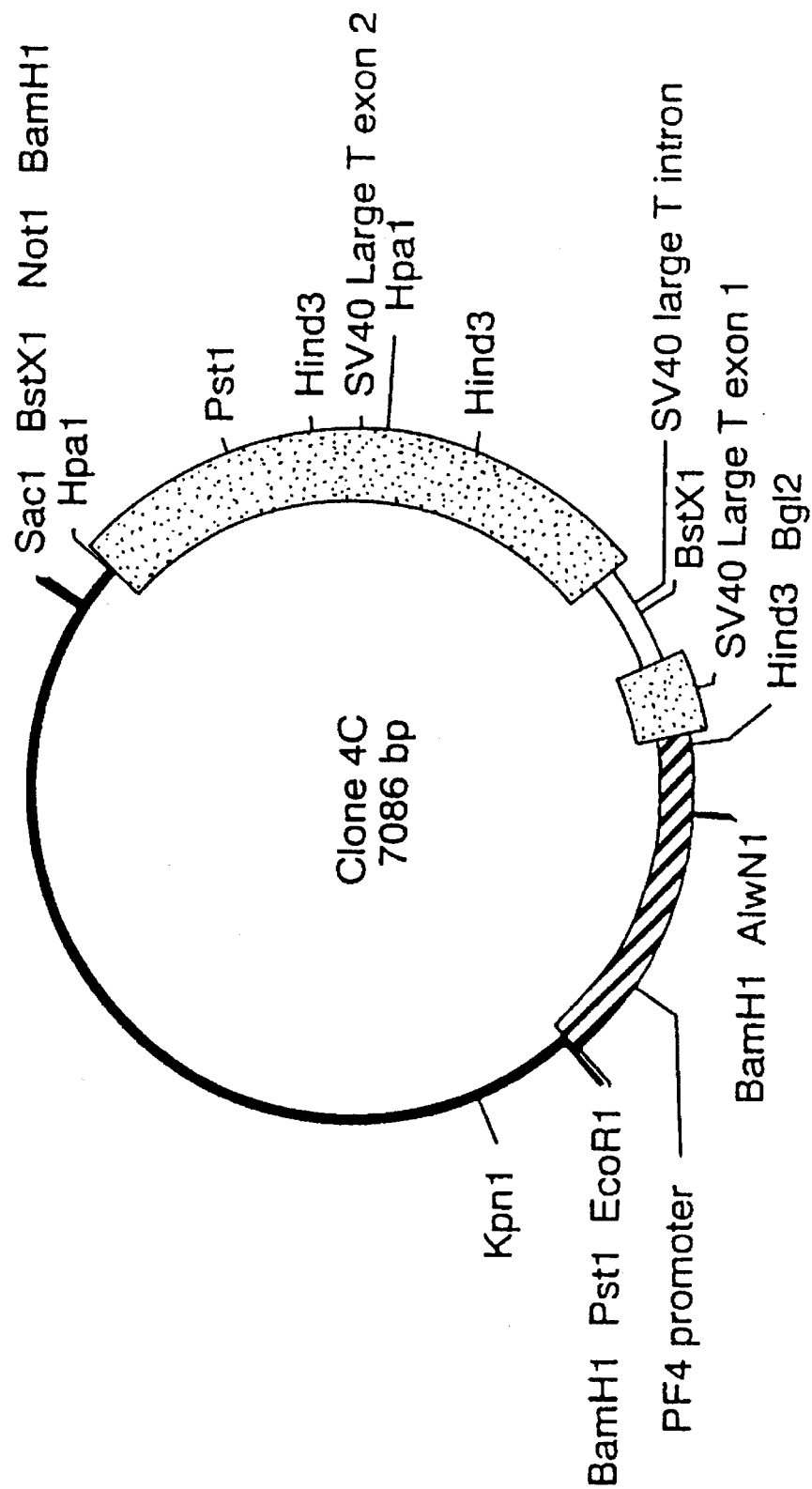
FIG. 1 is a diagramatic representation of the DNA construct integrated into the genome of transgenic mice. The sequence comprises about 1.1 kb of the Sprague-Dawley rat PF4 promoter sequence linked to the early region of the tsA58 mutation of SV40 viral genome.

The following terms, as defined below, are used to describe the invention:

As used herein, the term "vector" refers to nucleic acid sequences, arranged in such an order and containing appropriate components such that they are taken up into cells or can be inserted into cells through microinjection or other techniques. Such sequences may or may not naturally be present in the cell, either in whole or in part. Typically, the vector contains a promoter or promoters, a structural gene of interest that is to be transferred and expressed in the cell or organism (host) transfected with the vector, and other elements necessary for gene transfer and/or expression in the host such as sequences enabling the processing and translation of the transcription seuences, including translation initiation and polyadenylation sequences. In the present invention, the vector used may be circular or linear, and is preferably linear for insertion into embryos to generate a transgenic mammal.

As used herein, the term "promoter" refers to a nucleic acid sequence that regulates the transcription of its corresponding nucleic acid coding sequence or structural gene. The term "promoter" in the context of the present invention may include enhancer, repressor, transcription initiation site(s) and other such elements involved in the overall functioning of the promoter in regulating transcription of the corresponding structural gene. Preferred promoters of this invention include those promoters primarily active in platelet precursor cells, megakaryocytes, and/or megakaryocyte precursor cells such as, for example, the PF4 promoter (Ravid et al., 1992, supra), and the MPL promoter (Wendling et al., *Blood* 80:246a [1992]).

As used herein, the term "operably linked" refers to the orientation of the promoter with respect to the structural gene(s) of interest along the vector. The promoter is placed in such a position that it is capable of controlling or regulating the expression of the structural gene(s).

The terms "platelet precursor promoter" and "megakaryocyte promoter" refer to promoters that are active, (i.e., capable of driving expression of the structural genes to which they are operably linked), primarily in platelet precursor cells and/or megakaryocytes and megakaryocyte progenitor cells. Such promoters may exhibit minimal activity in other tissues or cell types.

The term "transgene" refers to a gene that is (1) either not naturally found in the mammal to be genetically manipulated; (2) is a mutant form of a gene naturally found in the mammal; (3) is a gene that serves to add additional copies of the same or a similar gene that is found in the mammal; (4) is a gene directed to be expressed in an abnormal lineage of cells; or (5) is a silent endogenous gene whose expression is induced. By "mutant form" is meant a gene that contains one or more nucleotides in the gene sequence that are different from, i.e., substitutes for, the wild-type or natural sequence; alternatively, or additionally, the gene may contain nucleotide insertions or deletions.

The terms "SV40 tsA58 early region", "SV 40 T antigen", and "tsA58 mutant" refer to the nucleic acid encoding the simian virus early region genes, where the large T antigen encoded in the early region nucleic acid sequence contains a mutation, the tsA58 mutation, resulting in an altered activity as compared to the naturally occurring, wild-type large T antigen gene, as described by Tegtmeyer, *J. Virol.*, 15:613–618 [1975]. As used herein, these terms may be used interchangably to infer either the large T antigen sequence of the SV40 early region, or the entire early region sequence.

The term "mammal" refers to all non-human animals that belong to the class mammalia. Preferably, the term includes all members of the class mammalia except humans. More preferably, the term includes all strains of rodents such as rabbits, rats, mice, and hamsters. Especially preferred for use in the invention are rats, hamsters and mice. Most preferred are mice, especially those strains that provide high nuclear yield, good pronuclear visibility, good in vitro viability, and good reproductive fitness in the adult, i.e., those considered to be healthy.

The terms "progeny" and "progeny of the transgenic mammal" refer to any and all offspring of every generation subsequent to the originally transformed mammals.

The terms "founder line", "founder mice" and "founders" refer to those mammals that are the mature product of the embryos to which the transgene was added by microinjection or by other technique, i.e., those mammals that grew from the embryos into which DNA was inserted, and that were implanted into one or more surrogate hosts.

The term "thrombocytopenia" refers to a decreased platelet count in the blood relative to a normal platelet count. Such a decrease is meant herein to include any level below that determined as normal for the particular mammalian species of interest. Thrombocytopenia may appear at any stage of the mammal's development, and may be temporary or permanent. Where temporary, the disease may reappear at any time in the lifecycle of the mammal. Thrombocytopenia may or may not be inherited by the offspring of those mammals affected with it.

The terms "megakaryocyte leukemia" and "megakaryocytic leukemia" describe a condition wherein a cell or cells of the mammal divide in an uncontrolled manner, resulting in a pathological state. Such cells express markers of the megakaryocyte lineage including, without limitation, the markers designated as platelet factor 4, von Willebrand factor, and other proteins immunoreactive with antisera produced against platelets. In addition, such cells may be morphologically identifiable as megakaryocytes using standard criteria to identify such cells.

The term "mammalian cell line" refers to cells derived from tissues or tumors of mammals that are able to survive and/or divide under appropriate culture conditions. As used herein, this term includes all successive generations of the cells originally derived from tissues or tumors.

The term "fertilized mammalian embryo" refers to the early zygote, especialy a single cell, resulting from the fusion of an oocyte and a sperm.

The terms "surrogate host" and "surrogate mother" may be used interchangably, and refer to a mammal, preferably a female, that is implanted with a fertilized embryo into which transgene(s) have been introduced. The surrogate host is typically of the same or a similar species as the embryo, and is receptive to the embryos by appropriate treatment with hormones where necessary and/or copulation with a vasectomized male. As used herein, however, the terms are meant to include also a test tube, dish, and/or incubator or other suitable instrument that may be used as a receptacle for embryo maturation and development, either as a substitute for, or in addition to implantation of the embryo into a mammal of the same or similar species.

A. Preparation of Constructs for Transformation

1. Selection of Transgene

The transgene of interest is selected for its ability to affect cell cycle control and regulation, and/or its ability to promote growth and/or division of cells. The simultaneous use of more than one transgene for insertion into a single embryo is within the scope of this invention. A gene(s) that alters platelet levels in the mammal into which it is introduced, and/or in the offspring of such mammals is the preferred transgene(s) herein. The structural gene may be obtained from any source, including viral, unicellular prokaryotic or eukaryotic organisms, vertebrate or non-vertebrate mammals, or plants. If obtained from vertebrate mammals, the structural gene may be from a homologous source (i.e., a gene from one mouse implanted into another mouse), or from a non-homologous source (i.e., a structural gene from rabbit implanted into a mouse). The transgene may have additional effects on the phenotype of the transgenic mammal, and these effects may be related or unrelated to platelet levels. Preferred transgenes for use in the present invention include myc, myb, E2F (Nevins, J. R., Science 258:424–429 [1992]), abl, ras, pim.1, src, E1A (Nevins, supra), HPVE7 (human papilloma virus E7, Nevins, supra), and SV40 early region, SV40 large T antigen, SV40 large T antigen tsA58 mutant, and mutants and fragments thereof. More preferred genes include myc, E2F, SV40 early region, and the SV40 early region tsA58 mutant. The most preferred gene is SV40 early region tsA58 mutant.

2. Selection of Promoter

Promoters useful in practicing this invention are those that are highly regulated with respect to activity, both temporally and spatially. Thus, the promoters of choice are those that are active only in particular tissues or cell types, preferably platelets, platelet precursor cells, and/or megakaryocytes. The source of the promoter may be from any unicellular prokaryotic or eukaryotic organism, any vertebrate or invertebrate, or any plant. Where the promoter is obtained from a mammal, the mammal may be homologous (the same species as the mammal to be transfected) or non-homologous (a different species). Preferred promoters of this invention are those expressed primarily in platelets and platelet precursors such as megakaryocytes. Preferred for use in the present invention are the PF4 promoter, the alpha-IIB integrin promoter (Marguerie et al., 7th International Symposium on the Biology of Vascular Cells, p. 18, San Diego, Calif. [1992]), the glycoprotein GPIIb promoter (Uzan et al., J. Biol. Chem., 266:8932–8939 [1991]), the platelet glycoprotein GPIb promoter (Wenger et al., Biochem. Biophys. Res. Comm., 166:389–395 [1988]), the promoter of the M2PTP gene (Plutzsky et al., Proc. Nat'l. Acad. Sci. USA, 89:1123–1127 [1992]) and the MPL promoter (Wendling et al., Blood, 80:246a [1992]), all of which may be obtained from any source. Most preferred is the rat PF4 promoter.

3. Other Vector Components

In addition to a promoter and one or more structural genes, the vectors of this invention preferably contain other elements useful for optimal functioning of the vector in the mammal into which the vector is inserted. These elements are well known to those of ordinary skill in the art, and are described, for example in Sambrook et al., Molecular Cloning: A Laboratory Manual Cold Spring Harbor Laboratory Press, 1989.

4. Construction of Vectors

Vectors used for transforming mammalian embryos are constructed using methods well known in the art, including, without limitation, the standard techniques of restriction endonuclease digestion, ligation, plasmid and DNA and RNA purification, DNA sequencing, and the like as described, for example in Sambrook, Fritsch, and Maniatis, eds., Molecular Cloning: A Laboratory Manual., (Cold Spring Harbor Laboratory Press, Cold Spring Harbor, N.Y. [1989]).

A preferred vector for use in the invention is plasmid 4C, illustrated in FIG. 1, and deposited in the ATCC, as noted below.

B. Production of Transgenic Mammals

The specific lines of any mammalian species used to practice this invention are selected for general good health, good embryo yields, good pronuclear visibility in the embryos, and good reproductive fitness. For example, when transgenic mice are to be produced, lines such as C57/BL6 x DBA2 F1 cross, or FVB lines are used (obtained commercially from Charles River Labs).

The age of the mammals that are used to obtain embryos and to serve as surrogate hosts is a function of the species used, but is readily determined by one of ordinary skill in the art. For example, when mice are used, pre-puberal females are preferred, as they yield more embryos and respond better to hormone injections.

Similarly, the male mammal to be used as a stud will normally be selected by age of sexual maturity, among other criteria.

Administration of hormones or other chemical compounds may be necessary to prepare the female for egg production, mating, and/or reimplantation of embryos. The type of hormones/cofactors and the quantity used, as well as the timing of administration of the hormones will vary for each species of mammal. Such considerations will be readily apparent to one of ordinary skill in the art.

Typically, a primed female (i.e., one that is producing eggs that can be fertilized) is mated with a stud male, and the resulting fertilized embryos are then removed for introduction of the transgene(s). Alternatively, eggs and sperm may be obtained from suitable females and males and used for in vitro fertilization to produce an embryo suitable for introduction of the transgene.

Normally, fertilized embryos are incubated in suitable media until the pronuclei appear. At about this time, exogenous nucleic acid comprising the transgene of interest is introduced into the female or male pronucleus. In some species such as mice, the male pronucleus is preferred.

Introduction of nucleic acid may be accomplished by any means known in the art such as, for example, microinjection. Following introduction of the nucleic acid into the embryo, the embryo may be incubated in vitro for varying amounts of time, or reimplanted into the surrogate host, or both. In vitro incubation to maturity is within the scope of this invention. One common method is to incubate the embryos in vitro for 1–7 days and then reimplant them into the surrogate host.

Reimplantation is accomplished using standard methods. Usually, the surrogate host is anesthetized, and the embryos are inserted into the oviduct. The number of embryos implanted into a particular host will vary, but will usually be comparable to the number of offspring the species naturally produces.

Transgenic offspring of the surrogate host may be screened for the presence of the transgene by any suitable method. Screening is often accomplished by Southern or Northern analysis, using a probe that is complementary to at least a portion of the transgene. Western blot analysis using an antibody against the protein encoded by the transgene may be employed as an alternative or additional method for screening. Typically, the tissues or cells believed to express the transgene at the highest levels are tested, although any tissues or cell types may be used for this analysis.

Alternative or additional methods for evaluating the presence of the transgene include, without limitation, suitable biochemical assays such as enzyme and/or immunological assays, histological stains for particular markers or enzyme activities, and the like. Blood cell count data is useful for evaluation of thrombocytopenia.

Progeny of the transgenic mammals may be obtained by mating the transgenic mammal with a suitable partner, or by in vitro fertilization of eggs and/or sperm obtained from the transgenic mammal. Where in vitro fertilization is used, the fertilized embryo may be implanted into a surrogate host or incubated in vitro, or both. Where mating is used to produce transgenic progeny, the transgenic mammal may be backcrossed to a parental line. Using either method, the progeny may be evaluated for the presence of the transgene using methods described above, or other appropriate methods.

The transformed mammals, their progeny, and cell lines of the present invention provide several important uses that will be readily apparent to one of ordinary skill in the art. The mammals and cell lines are particularly useful in screening compounds that have potential as prophylactic or therapeutic treatments for thrombocytopenia and/or megakaryocyte leukemia.

In the case of transgenic mammals, screening of candidate compounds is conducted by administering the compound(s) to be tested to the mammal, over a range of doses, and evaluating the mammal's physiological reponse to the compound(s) over time. Administration may be oral, or by suitable injection, depending on the chemical nature of the compound being evaluated. In some cases, it may be appropriate to administer the compound in conjunction with co-factors that would enhance the efficacy of the compound.

In screening cell lines for compounds useful in treating thrombocytopenia and/or megakaryocytic leukemia, the compound is added to the cell culture medium at the appropriate time, and the cellular response to the compound is evaluated over time using the appropriate biochemical and/or histological assays In some cases, it may be appropriate to apply the compound of interest to the culture medium in conjunction with co-factors that would enhance the efficacy of the compound.

The invention will be more fully understood by reference to the following examples. They should not be construed in any way as limiting the scope of the present invention.

EXAMPLES

A. Platelet Factor 4 (PF4) Promoter Cloning

An ~1.1 kb fragment of the 5' region of the platelet factor 4 ("PF4") gene from a Sprague-Dawley genomic DNA library was cloned by polymerase chain reaction (PCR) amplification using the complementary oligonucleotides (SEQ ID No: 2) GCTTGAATTCCTTTACTCTGCG for the 5' (distal end) and (SEQ ID No.: 3) GGAATTCAAGCTTGATATCCAAGGGCTACCTCGG for the 3' (proximal end). The resulting DNA fragment was digested with EcoRI restriction endonuclease and the overlapping end of the DNA was made blunt with the Klenow fragment of DNA polymerase using standard methods. This fragment was cloned into the vector pBluescript II KS+ (Stratagene, La Jolla, Calif.) by digesting the pBluescript vector with the restriction endonuclease EcoRV and ligating the insert and the vector with DNA ligase. The resulting clones were isolated and transformed into $E.\ coli$ DH5α cells for plasmid amplification. Plasmid was purified from the cells using the standard alkaline lysis method. This clone was designated plasmid "4A". More than 20 differences between the published sequence from Fisher rat (Ravid et al. [1991], supra) and the sequenced clone were identified. These differences are identified in FIG. 4.

B. tsA58 SV40 Cloning

A DNA fragment generated by KpnI and BamHI restriction enzyme digestion containing the wild-type SV40 virus early region was ligated into the pBluescript II KS+ vector previously digested with the restriction endonucleases KpnI and BamHI. This ligated vector containing the SV40 insert was then digested with HpaI, removing a DNA fragment of ~1.1 kb from position 3733 to 2666 of the SV40 early region. The same fragment from an SV40 clone containing the tsA58 mutation (Alanine to Valine at position 3505) described by Tegtmeyer, supra, was ligated into the vector. The resulting vector was transformed into $E.\ coli$ DH5α cells for plasmid amplification. The desired plasmid was isolated from these cells and was designated plasmid "4B".

C. PF4/tsA58 SV40 Fusion Gene

The 4A clone described above was digested with restriction enzymes EcoRV and SpeI, and the ~1.1 kb fragment of the PF4 promoter containing fragment was isolated using standard methodology. The overlapping end of this promoter fragment was blunted with the Klenow fragment of DNA polymerase using standard techniques. Clone 4B was linearized at position 5187 with the restriction enzyme AyrII, blunted with the Klenow fragment of DNA polymerase, and the PF4 promoter containing fragment was ligated into the site so that the direction of transcription of the PF4 promoter was the same as for the SV40 early region structural gene. The PF4 promoter containing sequence is shown in FIG. 2. This clone was designated plasmid "4C". The resulting fusion gene was isolated from vector sequences with restriction enzymes NotI and EcoRI and injected into fertilized mouse embryos. Plasmid 4C is deposited at the ATCC in transformed *E. coli* DH5α cells and is available under the accession number ATCC 69182.

D. Preparation of Embryos and Microinjection

Pregnant mare's serum ("PMS"), supplying Follicle Stimulating Hormone ("FSH") was administered to female mice of the strain BDF2 (Charles River Labs) about three days prior to the day of microinjection. PMS (obtained from Sigma Chemicals) was prepared as a 50 I.U./ml solution in Phosphate Buffered Saline and injected interperitoneally at 0.1 ml (5 I.U.) per animal. Human Chorionic Gonadotropin ("HCG"), supplying Luteinizing Hormone ("LH") was administered 45–48 hours after the PMS injections. HCG was also prepared as a 50 I.U./ml solution in PBS and injected IP (intraperitoneally) at 0.1 ml per animal. Females were placed with stud males of the same strain immediately after HCG injections. After mating, the females were examined for a vaginal copulation plug. The appearance of an opaque white plug indicated a successful mating.

Successfully mated females were sacrificed by cervical dislocation, and both oviducts were rapidly removed and placed in M2 medium (Hogan et al., eds., *Manipulating the Mouse Embryo: A Laboratory Manual,* Cold Spring Harbor Laboratory Press, pp 249–257 [1986]). The oviducts were transferred individually from M2 medium to PBS containing 300 µg/ml hyaluronidase (Sigma Corp., St. Louis, Mo.) in a round bottom dissection slide. The embryos were teased out of the oviduct and allowed to settle at the bottom of the slide as the cumulus cells detached from the embryos. When the cumulus masses were disaggregated (about 5 minutes) the embryos were transferred through two washes of M2 medium and the fertilized embryos were separated from unfertilized and abnormal embryos. The fertilized embryos were then transferred through 5% $CO_2$ equilibrated M16 medium (Hogan et al., supra), placed in equilibrated microdrop dishes containing M16 medium under paraffin oil and returned to the incubator.

E. Injection Procedure

Fertilized embryos were selected in M16 medium and incubated about 5 hours at 37° C. until the pronuclei appeared. Embryos were then transferred into M2 medium in a shallow depression slide under paraffin oil and placed under the microscope. The pronuclei were easily visible under 200X magnification. Using suction on the holding piper, a single embryo was selected and rotated such that the male pronucleus was away from the holding piper. Approximately 2 picoliter of solution containing the DNA construct at about 1 microgram per ml was injected into the one of the pronuclei, preferably the male pronucleus. Following the injection, the embryos were returned to incubation for 18 hours and reimplanted the next day into foster pseudopregnant females (prepared as described below and in Hogan et al., supra, pp. 132–145).

F. Reimplantation

Reimplantations were performed on anaesthetized mice of strain C57/BL6 x DBA2 F1 cross using a dissecting microscope. A pseudo-pregnant female mouse was anaesthetized with 0.017–0.020 ml/g body weight of avertin, injected IP. The mouse was placed under the dissecting microscope and the incision area was disinfected with 70% ethanol. The ovary was exteriorized and the bursal sac that surrounds the ovary and the oviduct were carefully pulled open. The ovary and oviduct were separated to expose the opening of the oviduct (termed the infindibulum). Surviving embryos were then removed from the incubator and loaded into the reimplantation pipet. The tip of the pipet was inserted several millimeters into the infindibulum and gentle pressure was used to deliver the embryos into the oviduct. About 10 to 20 embryos were implanted per mouse, resulting in a litter size of 5 to 12. The ovary then was returned to the peritoneum, and the body wall and then the skin were sutured.

G. Identification of Transgenic Mice

Of 109 mice born after embryo injections, 20 contained the transgene as assayed by specific PCR amplification using the oligonucleotides described in Section A above. These results were confirmed by Southern analysis (Sambrook et al., [1989]) using a DNA probe generated from the oligonucleotides used for PCR analysis. These transgenic mice are termed the founder mice. Two of these mice died unexpectedly after tail biopsies, having bled profusely. The remaining 18 mice were bled by tail vein nick and the blood samples were placed into a tube containing EDTA powder.

H. Analysis of Blood Cell Content

Figure 3A:
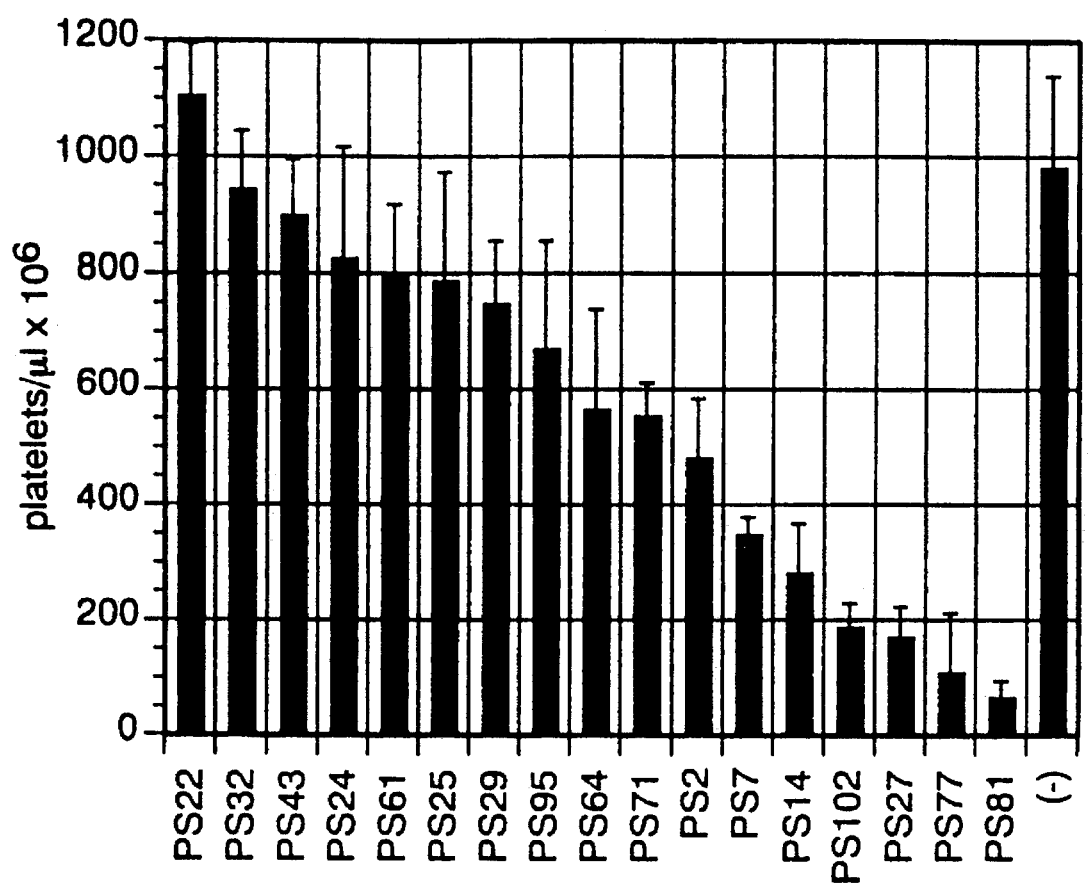
FIG. 3A depicts platelet counts of founder transgenic mice.

Blood cell content of each transgenic founder mouse was analyzed using a Sysmex TM Cell analyzer (TOA Medical Electronics, Kobe, Japan). Twenty microliters of blood obtained from each mouse was added to manufacturer's diluent for analysis. Platelet counts, white blood cell counts, red blood cell counts, and mean platelet volume were all obtained on that instrument. All blood cell parameters were within the range observed for the control (nontransgenic) littermate mice, except for the platelet counts. Normal platelet counts for mice are 800,000–1,200,000 platelets per microliter of blood. Platelet counts of the transgenic mice are shown in FIG. 3A. As is apparent, founder mice PS14, PS27, PS77, PS81, and PS102 had platelet levels that were 5–25% of the controls; founder mice PS2, PS7, PS64, PS71, and PS95 had platelet levels that were 25–60% of the controls; and mice PS22, PS24, PS25, PS28, PS29, PS32, PS43, and PS61 had platelet levels that were comparable to the levels of the control mice. Thus, the majority of the transgenic mice had thrombocytopenia.

I. Production of F1 Generation Mice

To determine whether the platelet phenotype was directly correlated with the presence and activity of the transgene construct, hemizygous F1 generation transgenic mice were derived from all lines except PS28, PS43, and PS61. The F1 generation was prepared by backcrossing each line to the C57/BL6 xDBA2 F1 cross mouse line.

A RNA/DNA hybridization assay (Hunt et al., *Blood* 80: 904–911 [1992]) was performed on DNA obtained from tail tissue of each mouse. This assay used both SV40 T antigen and mouse stem cell factor (SCF) RNA probes. The ratio between the T antigen signal and the SCF signal was used to determine the zygosity of the mice. Blood analysis was obtained for each mouse using the Sysmex TM system as described above.

To assay the level of megakaryocytes in the transgenic F1 population, bone marrow cells were obtained from lines PS2, PS7, PS14, PS22, PS25, PS29, PS32, and PS77. The bone marrow cells were obtained by flushing marrow from the longbones of the hind legs using Levine's CATCH buffer (Levine, A. and Fedorko, M. *J. Cell Biol.*, 69:159 [1976]). These cells were stained for acetylcholinesterase, a marker for megakaryocytes (Burstein et al., *J. Cell. Physiol.*, 122:159–165 [1985]) and with May-Gruenwald Giesma stain. The results are shown in FIG. 3C. As is apparent, there is a trend towards an inverse correlation between platelet count in the blood and megakaryocyte cell count in the bone marrow.

In addition, the spleens from these mice were dispersed and stained for acetylcholinesterase activity, and line PS14 was observed to contain about four times the number of acetylcholinesterase positive staining cells as observed in the control mice.

Examination of peripheral blood smears from lines PS2, PS7, PS14, and PS77 indicated reduced platelet levels as compared to controls, and also revealed the presence of large agranular platelets. Bone marrow smears from the same lines indicated an abnormal shape and size of the megakaryocytes.

J. Production of F2 Generation Mice

Figure 3B:
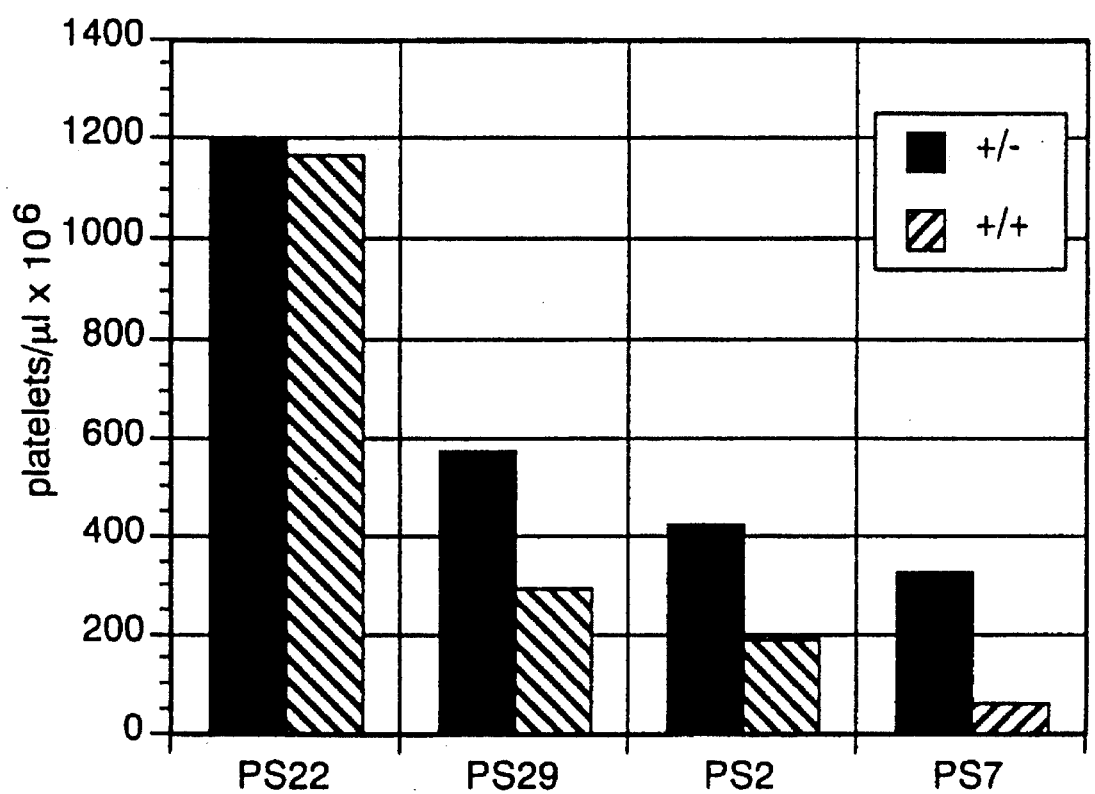
FIG. 3B shows platelet counts of F2 mice hemizygous or homozygous for the transgene.

To examine the effect of gene dosage on the platelet phenotype, hemizygous F1 mice were bred together and mice homozygous for the transgene were identified for lines PS2, PS7, PS22, and PS29. Platelet counts were obtained for these mice. The platelet counts are shown in FIG. 3B where the solid boxes indicate hemizygosity for the transgene, and hatched boxes indicate homozygosity for the transgene. With the exception of line PS22, the homozygous mice exhibited a more severe platelet deficiency phenotype than did the hemizygous mice.

K. Identification of Megakaryocyte Leukemia

The cause of death of various transgenic mice was determined. Tissues from the PS22 line founder mouse were fixed and sectioned, and the presence of leukemic cells was observed in liver, intestine, and spleen; many of the cells tested stained positive with a polyclonal antibody directed against mouse platelets, and the nuclei of the leukemic cells were immunoreactive for an antibody to SV40 T antigen.

In addition, mice of lines PS14, PS24, and PS71 died before eight months of age. Necropsy of these animals revealed grossly enlarged spleens and mottled livers, suggesting a leukemic pathology.

L. Production of Cell Lines

Transgenic mice are examined for a moribund appearance, indicating imminent death. When such features as ruffled fur, decreased activity level, swollen abdomen, and/or a palpable spleen are observed, the mice are euthanized and the spleen, bone marrow, and lymph node tissues are removed. The tissues are immediately dispersed into suitable media such as RPMI 1640 containing a serum supplement such as fetal calf serum at 5–25% (v/v), and appropriate growth factors including, without limitation, interleukin 3 and/or stem cell factor at appropriate levels. Incubation of the cells is at 33° C., 37° C. or 39° C. The culture medium is changed regularly. After suitable time has elapsed for the cells to separate, the cells are assayed for the presence of megakaryocyte and/or platelet markers such as acetylcholinesterase (for megakaryocytes).

DEPOSITS

Plasmid 4C containing the Sprague-Dawley rat PF4 promoter linked to SV40 early region tsA58 mutant was deposited in *E. coli* host cells, under the terms of the Budapest Treaty, with DH5α the American Type Culture Collection ("ATCC"), 12301 Parklawn Drive, Rockville, Md. 20852, on Jan. 7, 1993. Samples of these cells are available to one skilled in the art under the accession number ATCC 69182.

All literature cited herein is specifically incorporated by reference.

We claim:

1. A vector comprising a nucleic acid molecule encoding the SV40 early region tsA58 mutant operably linked to a rat PF4 promoter.

2. A mouse expressing a transgene stably incorporated into its DNA, wherein the transgene comprises the DNA encoding the SV40 early region tsA58 mutant operably linked to a rat PF4 promoter, and expression of the transgene causes thrombocytopenia or megakaryocyte leukemia.

3. A method of preparing a mouse with thrombocytopenia, comprising:
   a) introducing into a fertilized mouse embryo a DNA molecule encoding the SV40 early region tsA58 mutant operably linked to a rat PF4 promoter;
   b) implanting said embryo into a surrogate mother to produce offspring; and
   c) screening said offspring for decreased platelet counts.

4. The method of claim 3 wherein the nucleic acid molecule is introduced into embryos using 5. A method of preparing a mouse with megakaryocyte leukemia, comprising:
   a) introducing into a fertilized mouse embryo a DNA molecule encoding the SV40 early region tsA58 mutant operably linked to a rat PF4 promoter;
   b) implanting said embryo into a surrogate mother to produce offspring; and
   c) screening said offspring for megakaryocyte leukemia.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1264 base pairs
        ( B ) TYPE: Nucleic acid
        ( C ) STRANDEDNESS: Single stranded
        ( D ) TOPOLOGY: Linear ( x i ) SEQUENCE DESCRIPTION: SEQ ID NO:1:

```
TTGGAGCTCC   ACCGCGGTGG   CGGCCGCTCT   AGAACTAGTG   GATCCCCGG            50

GCTGCAGGAA   TTCGATAATT   CCTTTACTCT   GCGAATGCTG   AAATCTTTGG          100

TGAAGGTGGC   ACAGAAGAGT   TTTCTTGCTG   TCCAGATTAA   AATCCTCTTA          150

TCATATATAT   ATATATATAT   ATATATATAT   GTATATATAT   ATATTTATTT          200

TTTTATTTTT   ATTTTTTTTT   TTTTTGCTG    ACCAGCCGA    GGCCTTGAGT          250

TTCAGTTCCC   TAAAGGCATA   GGGATTCTGA   CATGTTTTGC   AGTAGCCGTT          300

GTTGTCCATG   CTGAGTGTCC   ATAAATGTAT   GCCCCGGGGA   GTTATGCTTG          350

ACTATATCAC   TATGCATGGG   GGGCAGATAA   AGGGGCACAT   AATTATAACC          400

ATATATGGCA   TGAATTAATA   TAGAGATCTC   CAACTGTCCC   AGAAAGCTTT          450
```

| | | | | | |
|---|---|---|---|---|---|
| CTTCTCTACT | CTTCTCCAGG | GTAGAGCTGA | GCAGACTAAA | AGATTTTTAT | 500 |
| CAAAGAAAAG | CCTTCAAATA | CTACCTCAGG | GATGTTTCTA | AAGAGTCCTG | 550 |
| AGAAGAGCAG | ACCCTGCCGC | CTCCAGTAGA | TTGGACAGCC | GTAGCTCAGA | 600 |
| AGAGCCTCCA | GAATTTCCTG | CAGGAGGCTT | CGGAAGGTTT | CCATCGTGAG | 650 |
| GATGAAAGTC | AGAAGCCATT | GCCTAGCCAT | TCACTTCAAT | GTTTTAATGG | 700 |
| CAGAAAATAA | ATTTCCAGTC | TCGCATCTCT | AACCACATGG | CAGTCAAACT | 750 |
| CACAGCAAAT | CAACAGGAAG | CACGGCAGGG | TGTTTGGGGT | AGGGCAACCG | 800 |
| GAAGTCGGGA | AGGCAACAAA | TTGGTACTGA | AGGTGCATGT | TCTGTAAACC | 850 |
| GCATGGGGAT | AGCAGAAAAT | TCTCTGCCAC | ATACAGCATA | CCTTCTGCGA | 900 |
| AAATTCCAAC | TGTTTCTACC | TCTGTAGACT | GTTCACATAA | ATTCACATTG | 950 |
| GGGACGTGGA | TCCTGCTGAC | AGCTGCTGAC | AGCTGGCCTC | AGCTGCTGCT | 1000 |
| TCTTCTTCTT | CTTCTTTTTT | TTTTTTTTT | TTTCCTGTTC | TATGTTGCTT | 1050 |
| TAATCTTGGC | TGGCCAGATC | TCAAGTACTG | TTCCACAAGT | GTCATTGCTT | 1100 |
| CTGTGGATCA | CTTCCTCATC | CCCTATCCCG | GGTTCCGGA | CTGGGCTGGC | 1150 |
| AGTGAAGATA | AACGTGTCT | AGAAAGTCAC | AGGAGCCACT | GTCTGGCACT | 1200 |
| TAGAGCCCCA | GACCCCAGTT | TCCCCGAGGT | AGCCCTTGGA | TATCAAGCTT | 1250 |
| GAATTATCAA | GCTT | | | | 1264 |

( 2 ) INFORMATION FOR SEQ ID NO:2:

( i ) SEQUENCE CHARACTERISTICS:
        ( A ) LENGTH: 22 base pairs
        ( B ) TYPE: Nucleic acid
        ( C ) STRANDEDNESS: Single stranded
        ( D ) TOPOLOGY: Linear ( x i ) SEQUENCE DESCRIPTION: SEQ ID NO:2:

| | | |
|---|---|---|
| GCTTGAATTC | CTTTACTCTG | CG | 22 |

( 2 ) INFORMATION FOR SEQ ID NO:3:

( i ) SEQUENCE CHARACTERISTICS:
        ( A ) LENGTH: 34 base pairs
        ( B ) TYPE: Nucleic acid
        ( C ) STRANDEDNESS: Single stranded
        ( D ) TOPOLOGY: Linear ( x i ) SEQUENCE DESCRIPTION: SEQ ID NO:3:

| | | | |
|---|---|---|---|
| GGAATTCAAG | CTTGATATCC | AAGGGCTACC | TCGG | 34 |

( 2 ) INFORMATION FOR SEQ ID NO:4:

( i ) SEQUENCE CHARACTERISTICS:
        ( A ) LENGTH: 1160 base pairs
        ( B ) TYPE: Nucleic acid
        ( C ) STRANDEDNESS: Single stranded
        ( D ) TOPOLOGY: Linear ( x i ) SEQUENCE DESCRIPTION: SEQ ID NO:4:

| | | | | | |
|---|---|---|---|---|---|
| AATTCCTTTA | CTCTGCGAAT | GCTGAAATCT | TTGGTGAAGG | TGGCACAGAA | 50 |
| GAGTTTTCTT | GCTGTCCAGA | TTAAAATCCT | CTTATCATAT | ATATATATAT | 100 |
| ATATATATAT | ATATGTATAT | ATATATATTT | ATTTTTTTAT | TTTTATTTTT | 150 |
| TTTTTTTTTT | GCTGACCCAG | CCGAGGCCTT | GAGTTTCAGT | TCCCTAAAGG | 200 |

| | | | | | |
|---|---|---|---|---|---|
| CATAGGGATT | CTGACATGTT | TTGCAGTAGC | CGTTGTTGTC | CATGCTGAGT | 250 |
| GTCCATAAAT | GTATGCCCCG | GGGAGTTATG | CTTGACTATA | TCACTATGCA | 300 |
| TGGGGGGCAG | ATAAAGGGGC | ACATAATTAT | AACCATATAT | GGCATGAATT | 350 |
| AATATAGAGA | TCTCCAACTG | TCCCAGAAAG | CTTTCTTCTC | TACTCTTCTC | 400 |
| CAGGGTAGAG | CTGAGCAGAC | TAAAAGATTT | TTATCAAAGA | AAAGCCTTCA | 450 |
| AATACTACCT | CAGGGATGTT | TCTAAAGAGT | CCTGAGAAGA | GCAGACCCTG | 500 |
| CCGCCTCCAG | TAGATTGGAC | AGCCGTAGCT | CAGAAGAGCC | TCCAGAATTT | 550 |
| CCTGCAGGAG | GCTTCGGAAG | GTTTCCATCG | TGAGGATGAA | AGTCAGAAGC | 600 |
| CATTGCCTAG | CCATTCACTT | CAATGTTTTA | ATGGCAGAAA | ATAAATTTCC | 650 |
| AGTCTCGCAT | CTCTAACCAC | ATGGCAGTCA | AACTCACAGC | AAATCAACAG | 700 |
| GAAGCACGGC | AGGGTGTTTG | GGGTAGGGCA | ACCGGAAGTC | GGGAAGGCAA | 750 |
| CAAATTGGTA | CTGAAGGTGC | ATGTTCTGTA | AACCGCATGG | GGATAGCAGA | 800 |
| AAATTCTCTG | CCACATACAG | CATACCTTCT | GCGAAAATTC | CAACTGTTTC | 850 |
| TACCTCTGTA | GACTGTTCAC | ATAAATTCAC | ATTGGGGACG | TGGATCCTGC | 900 |
| TGACAGCTGC | TGACAGCTGG | CCTCAGCTGC | TGCTTCTTCT | TCTTCTTCTT | 950 |
| TTTTTTTTTT | TTTTTTTCCT | GTTCTATGTT | GCTTTAATCT | TGGCTGGCCA | 1000 |
| GATCTCAAGT | ACTGTTCCAC | AAGTGTCATT | GCTTCTGTGG | ATCACTTCCT | 1050 |
| CATCCCCTAT | CCCGGGTTTC | CGGACTGGGC | TGGCAGTGAA | GATAAAACGT | 1100 |
| GTCTAGAAAG | TCACAGGAGC | CACTGTCTGG | CACTTAGAGC | CCCAGACCCC | 1150 |
| AGTTTCCCCG | | | | | 1160 |

( 2 ) INFORMATION FOR SEQ ID NO:5:

( i ) SEQUENCE CHARACTERISTICS:
        ( A ) LENGTH: 1142 base pairs
        ( B ) TYPE: Nucleic acid
        ( C ) STRANDEDNESS: Single stranded
        ( D ) TOPOLOGY: Linear ( x i ) SEQUENCE DESCRIPTION: SEQ ID NO:5:

| | | | | | |
|---|---|---|---|---|---|
| AATTCCTTTA | CTCTGCGAAT | GCTGAAATCT | TTGGTGAAGG | TGGCACAGAA | 50 |
| GAGTTTTCTT | GCTGTCCAGA | TTAAAATCCT | CTTATCATAT | ATATATGTAT | 100 |
| ATATATATAT | ATATATATAT | ATATATTTTT | TTTTTTTTTT | TTTTTTTTT | 150 |
| TGCTGACCCA | GCCGAGGCCT | TGAGTTTCAG | TTCCCTAAAG | GCATAGGGAT | 200 |
| TCTGACATGT | TTTGCAGTAG | CCGTTGTTGT | CCATGCTGAG | TGTCCATAAA | 250 |
| TGTATGCCCC | GGGGAGTTAT | GCTTGACTAT | ATCACTATGC | ATGGGGGGCA | 300 |
| GATAAAGGGG | CACATAATTA | TAACCATATA | TGGCATGAAT | TAATATAGAG | 350 |
| ATCTCCAACT | GTCCCAGAAA | GCTTTCTTCT | CTACTCTTCT | CCAGGGTAGA | 400 |
| GCTGAGCAGA | CTAAAAGATT | TTATCAAAGA | AAAGCCTTCA | AATACTACCT | 450 |
| CAGGGATGTT | TCTAAAGAGT | CCTGAGAAGA | GCAGACCCTG | CCGCCTCCAG | 500 |
| TAGATTGGAC | AGCCGTAGCT | CAGAAGAGCC | TCCAGAATTT | CCTGCAGGAG | 550 |
| GCTTCAGAAG | GTTTCCATCG | TGAGGATGAA | AGTCAGAAGC | CATTGCCTAG | 600 |
| CCATTCACTT | CAATGTTTTA | ATGGCAGAAA | ATAAATTTCC | AGTCACGCAT | 650 |
| CTCTAACCAC | ATGGCAGTCA | AACTCACAGC | AAATCAACAG | GAAAGCACGG | 700 |
| CAGGGTGTTT | GGGGTCGGGC | AACCGGAAGT | CGGGAAGGCA | ACAAATTGGT | 750 |

| | | | | |
|---|---|---|---|---|
| ACTGAAGGTG | CATGTTCTGT | AAACCGCATG | GGGATAGCAG | AAAATTCTCT | 800 |
| GCCACATACA | GCATACCTTC | TGCGAAAATT | CCAACTGTTT | CTACCTCTGT | 850 |
| AGACTGTTCA | CATAAATTCA | CATTGGGGAC | GTGGATCCTG | CTGACAGCTG | 900 |
| CTGACAGCTG | GCCTCAGCTG | CTTCTTTTTT | TTTTTTTTTT | TTTTTTTTTT | 950 |
| CCTGTTCTAT | GTTGCTTTAA | TCTTGGCTGG | CCAGATCTCA | AGTACTGTTC | 1000 |
| CACAAGTGTC | ATTGCTTCTG | TGGATCACTT | CCTCATCCCC | ATCCCGGGTT | 1050 |
| TCCGGACTGG | GCTGGCAGTG | AAGATAAAAC | GTGTCTAGAA | AGTCACAGGA | 1100 |
| GCCACTGTCT | GGCACTTAGA | GCCCCAGACC | CCAGTTTCCC | CG | 1142 |